United States Patent [19]
Brooks et al.

[11] 4,331,134
[45] May 25, 1982

[54] COMBINATION FOAM/BANDAGE DISPENSER FOR USE IN MAKING A MEDICAL CAST

[76] Inventors: William R. Brooks; Irving C. Heinzel, both of 139 W. Commercial, Addison, Ill. 60101

[21] Appl. No.: 225,861

[22] Filed: Jan. 16, 1981

[51] Int. Cl.³ .............................................. A61F 5/04
[52] U.S. Cl. ..................................................... 128/90
[58] Field of Search ................... 128/90, 89 R, 87 R, 128/83, 82, 155, 156; 206/389, 440; 221/208–210; 222/544, 545

[56] References Cited

U.S. PATENT DOCUMENTS

| | | | |
|---|---|---|---|
| 3,301,252 | 1/1967 | Mahoney, Jr. | 128/90 |
| 3,563,234 | 2/1971 | Umstead | 128/90 |
| 4,020,832 | 5/1977 | Kirkpatrick et al. | 128/90 |
| 4,153,052 | 5/1979 | Tsuk | 206/389 X |

Primary Examiner—John D. Yasko
Attorney, Agent, or Firm—John S. Fosse

[57] ABSTRACT

Dispensing apparatus for use in making a foam medical cast comprises a valved canister charged with foam-making chemicals, a rolled-up strip of bandage fabric, a yoke arrangement for holding and allowing rotation of the bandage roll and having a mount for securing the canister in rigid position, and a manually operable handle pivotally mounted to the yoke arrangement. The handle cooperates with the yoke arrangement in enabling the imposition of linear actuating force on the canister valve so that operation of the handle opens the valve, simultaneous transit of the yoke arrangement to unroll the bandage produces a medical cast preform of foam deposited on the outstretched bandage strip.

8 Claims, 7 Drawing Figures

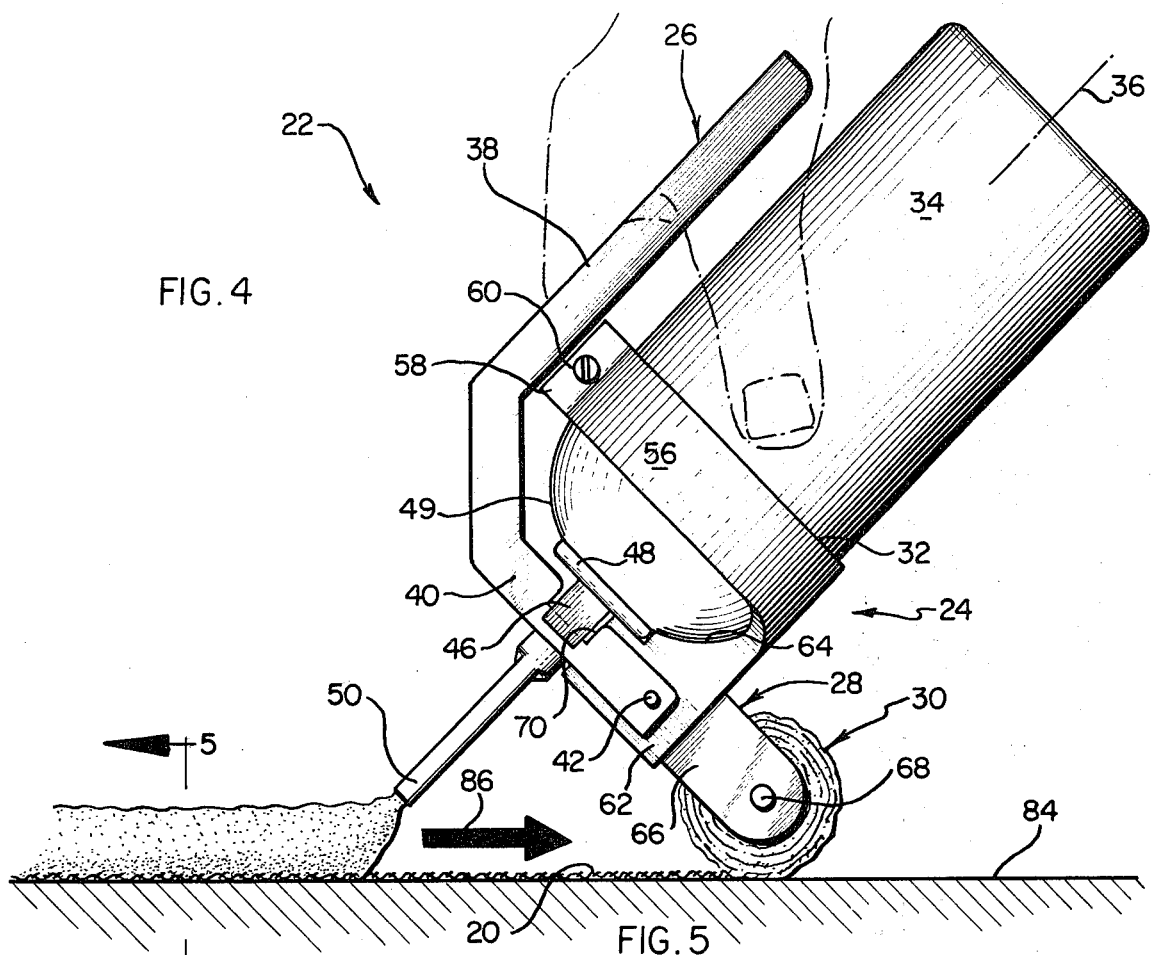
FIG. 4
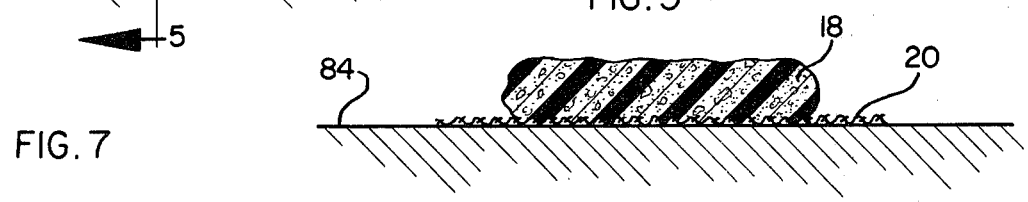
FIG. 5
FIG. 7
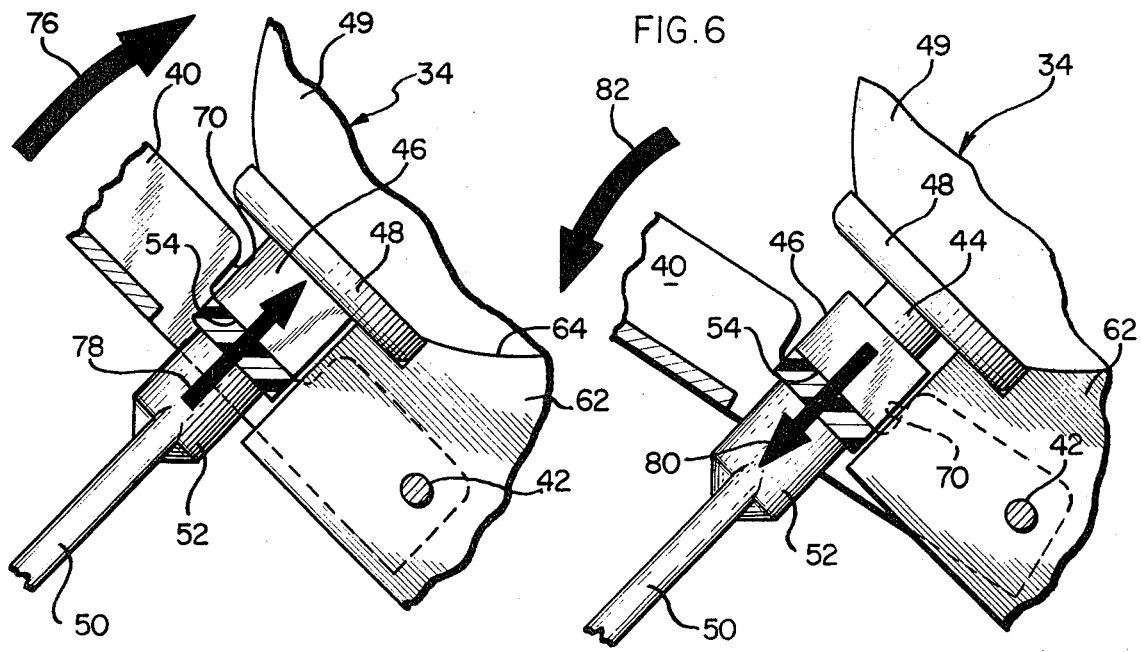
FIG. 6

COMBINATION FOAM/BANDAGE DISPENSER FOR USE IN MAKING A MEDICAL CAST

FIELD OF THE INVENTION

This invention relates generally to the fabrication of medical casts, more particularly to the making of urethane foam casts, and especially to apparatus for dispensing an incipiently curing polyurethane foam in the molding of a rigid, cellular plastic dressing.

BACKGROUND OF THE INVENTION

In the past, a number of different problems have frustrated the utilization of polyurethane foam as a medical cast material despite the clear advantages of such a composition for that purpose. One particularly vexing problem has centered on the difficulty of physically applying the comparatively fragile, uncured foam to the injured limb which is to be immobilized. Spraying of the foam directly onto the limb has presented obvious containment difficulties; and injection of incipiently curing foam into a tubular sleeve has resulted in a finished cast lacking the necessary uniformity of its physical properties.

BRIEF DESCRIPTION OF THE INVENTION

The instant invention contemplates dispensing apparatus which unrolls a length of fabric bandage onto a table or other horizontal support and simultaneously meters a band of incipiently curing polyurethane foam between the side edges of the bandage strip. During a short dwell time in contact with the bandage fabric, in order to permit an initial rise, the polyurethane foam becomes imbedded in the cloth material; and the resulting composite may then be easily handled as a flexible preform that is wrapped about the injured limb, shaped as desired, and allowed to complete its cure to a rigid, lightweight cast.

Accordingly, a general object of the present invention is to provide a new and improved dispensing apparatus for use in making a polyurethane foam medical cast.

Another object of the invention is to provide a combination foam/bandage dispenser which affords simple, one-hand operation.

Still another object of the invention is to provide a dispenser of the type described which is inexpensive and disposable.

These and other objects and features of the invention will become more apparent from a consideration of the following descriptions.

BRIEF DESCRIPTION OF THE DRAWINGS

The invention, both as to its structure and its mode of operation, will be better understood by reference to the following disclosure and drawings forming a part thereof, wherein:

FIG. 4 is a view of the dispensing apparatus of FIG. 3, shown in its dispensing mode making a foam medical cast preform;

FIG. 5 is a view taken in cross-section along the line 5—5 of FIG. 4 and showing placement of a band of incipiently curing polyurethane foam between the side edges of the bandage strip;

FIG. 6 is an enlarged view in partial section showing the canister valve actuating arrangement in its rest or neutral position; and FIG. 7 is a view similar to the showing of FIG. 6 but illustrating the valve actuating arrangement in operative condition imposing a substantially linear, valve-opening force on the canister valve.

DETAILED DESCRIPTION OF THE DISCLOSED EMBODIMENT

Figure 1:
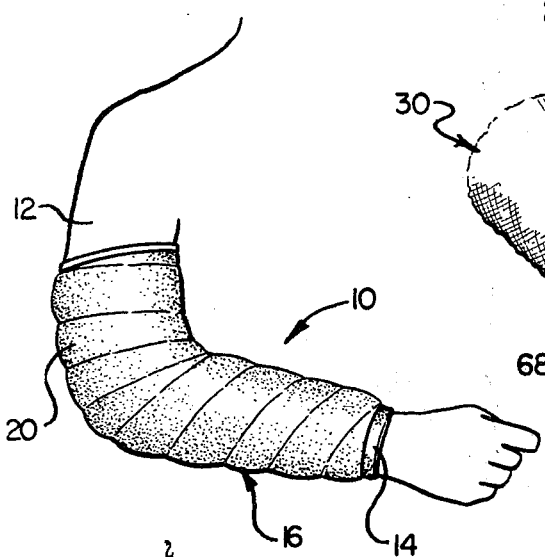
FIG. 1 is a perspective view showing a human patient with a full-arm medical cast which was made using dispensing apparatus according to the invention.
Figure 2:
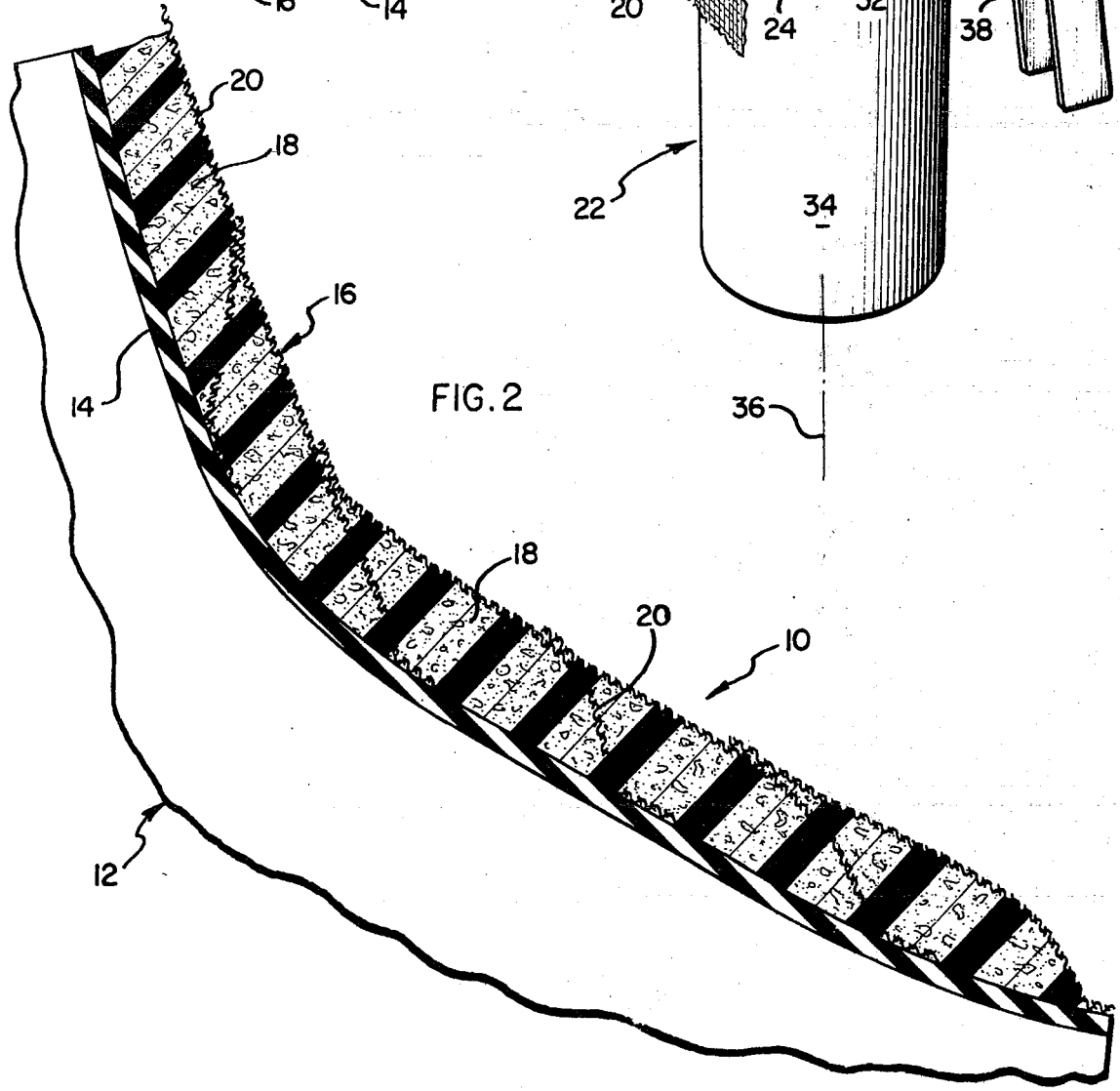
FIG. 2 is an enlarged view of a portion of the arm cast of FIG. 1 with the cast itself shown in cross-section.

Referring now in detail to the drawings, specifically to FIGS. 1 and 2, a finished polyurethane foam medical cast 10 is illustrated as having been applied to the upper and lower right arm 12 of a human patient. The cast 10 generally comprises a flexible, reticulated foam undergarment 14 and one or more spirally wrapped medical cast preforms 16. The preform or preforms 16 comprise a body or bead of polyurethane foam 18 and a bandage strip 20 which is disposed generally on the outer surface of the cast, the foam body 18 having become imbedded in the undergarment 14 and the bandage strip 20 as it cured, forming a monolithic structure. Details concerning the components and composition of the medical cast 10 are set forth in our co-pending application entitled "Foam Medical Cast" Ser. No. 178,567 which was filed on Aug. 15, 1980, now U.S. Pat. No. 4,309,990 which issued Jan. 12, 1982, and to which reference is made for completeness of the instant disclosure.

Figure 3:
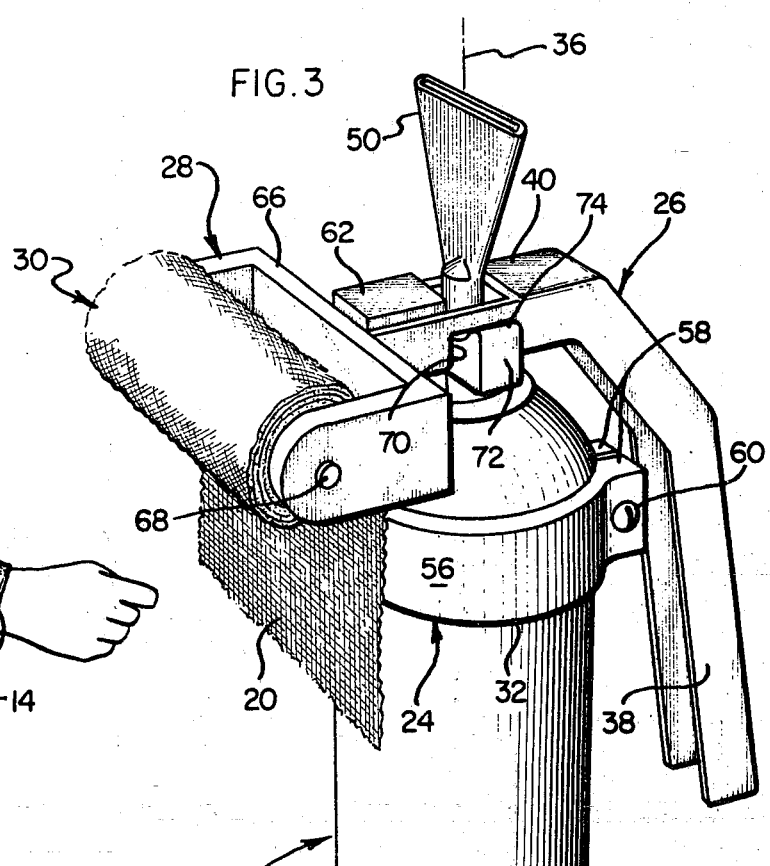
FIG. 3 is a perspective view of dispensing apparatus constructed in compliance with the principles of the present invention.

The present invention contemplates construction of the preforms 16 by means of dispensing apparatus which delivers a strip of bandage material and simultaneously applies a metered quantity of incipiently curing polyurethane foam to the unrolled bandage strip. With reference to FIGS. 3 and 4, dispensing apparatus 22 constructed in compliance with the invention comprises a yoke arrangement 24 and a manually operable handle 26. The yoke arrangement 24 includes a bearing unit 28 for holding and allowing rotation of a cylindrical bandage roll 30, and a mounting unit 32 for securing a foam chemicals canister 34 in substantially rigid position relative to the bearing unit 28 and aligned generally along a central, longitudinal axis 36. In order to provide dispensing apparatus which can be manipulated with only a single hand, as is suggested in FIG. 4, the manually operable handle 26 is fashioned to include a grip portion 38 and an offset portion 40, the grip portion 38 being disposed generally parallel with the axis 36 on one side thereof so that both may be grasped together in one hand. The offset portion 40 is pivotally connected to the yoke arrangement 24 on the opposite side of and spaced apart from the axis 36 by means of a pivot pin 42.

The canister 34 contains suitable quantities of a polyurethane prepolymer composition and liquified propellant gas for expelling that composition through a depressably actuatable valve unit 44 which is operated by a winged actuator cap 46 and which is secured in place by a mounting disc or plate 48, disc 48 being adapted to be crimped onto a raised rim or bead extending outwardly from the hemispherical domed top 49 of canister 34. The valve 44 selectively communicates the contents of the canister 34 with a fan-shaped discharge nozzle 50 which is conveniently made integral with the actuator cap 46. Advantageously, the wide dimension of the nozzle 50 is situated parallel with the axis of bandage roll 30 and generally transverse the strip of bandage material 20 which is unrolled in the course of generating the cast preforms, as is suggested in FIG. 4. Continuing with reference to FIGS. 6 and 7, the nozzle 50 has a tubular base or stem portion 52 which is coupled to the actuator cap 46 and which is of lesser diameter than the actuator cap in order to define an annular shoulder 54 for purposes to be described more fully hereinafter.

In order to secure the canister 34 in rigid relationship, the canister mounting unit 32 includes a circular strap portion 56 which is arranged for tightly embracing the cylindrical body of the canister 34 by means of arcuate convergible arms 58 and a screw 60 or other releasible fastening means. In addition, the canister mounting unit 32 includes a forwardly extending tongue 62 having a contoured section 64 which matably engages the confronting, dome-shaped region of the canister top 49, as is shown in FIG. 4, so as to promote positive coupling of the canister in the yoke arrangement 24.

The tongue 62 serves as a placement for the pivot pin 42 which acts as an attachment site for the swingable handle 26, tongue 62 further serves as the mounting for a C-shaped bandage yoke 66 of the bearing unit 28, as is best seen in FIG. 4. A removable axle 68 is journaled between the arms of the C-shaped yoke 66; and a strip of the bandage fabric 20 of suitable length and width is wound on a tubular core, or otherwise, to define the bandage roll 30 which is rotatably mounted by means of the axle 68. A suitable amount of frictional drag is built into the relationship between the bandage roll 30, the arms of yoke 66, and the axle 68 to insure uniform unrolling of the bandage strip during operation of the dispensing apparatus 22. In addition, removable mounting of the axle 68 simplifies replacement of the bandage roll when desired.

It is highly important to the development of a medical cast 10 of uniform thickness and strength that the dispensing apparatus 22 delivers a uniform bead of foam material 18 onto the bandage strip 20. Therefore and in compliance with an important feature of the present invention, the handle 26 is arranged to impose a substantially linear force on the canister actuating and dispensing valve 44. For this purpose, the offset portion 40 of handle 26 is fabricated with a centrally disposed notch 70 aligned with the axis of valve 44 and with the axis 36. As is shown in FIGS. 6 and 7, the notch 70 fittably receives the valve actuator cap 46 and acts against the shoulder 54. As is shown in FIG. 3, the actuator cap has integral, radially outwardly extending arms or wings 72 with raised tips 74 which serve to position the offset portion with respect to the actuator cap 46. Moreover, placement of the pivot pin 42 for the handle 26 on one side of the axis 36 and location of the grip portion 38 of the handle on the opposite side of that axis converts motion of the grip portion 38 generally toward the canister body in the direction of arrow 76 to a linearly inward force on the actuating valve in the general direction of arrow 78. Relaxation of manual gripping pressure on the handle portion 38 allows the compressed, internal rubber parts of the actuating valve to force the cap in the direction of the arrow 80 in FIG. 6 and movement of the offset portion 40 in the direction of arrow 82 and about the pivot axis of pin 42.

For purpose of affording a more complete understanding of the invention, it is advantageous now to provide a functional description of the mode in which the dispensing apparatus 22 operates.

With a full bandage roll 30 in place in the yoke arrangement 28 and with the canister 34 properly charged with polyurethane chemicals and propellant providing superatmospheric pressure within the canister, medical cast preforms 16 will be prepared by first clamping the free, leading end of the bandage strip 20 to one edge of a table or countertop 84 and advancing the dispensing apparatus 22 away from the clamped end and in the direction of arrow 86, as is shown in FIG. 4.

As the bandage strip 20 is being unrolled, the handle 26 is depressed toward the body of the canister 34 in the direction indicated in FIG. 7 by the arrow 76, thus applying linear inward force on the valve 44 to open the valve and release the polyurethane foam chemicals onto the bandage strip as the latter is laid out on the countertop 84. Because substantially linear force is imposed on the valve 44, the urethane chemicals are uniformly dispensed from the canister 34 and uniformly deposited on the bandage strip 20, forming an elongate body of incipiently curing foam of substantially uniform height and width, as is shown in FIG. 5. In addition, the pressure within the canister 32 is coordinated with the diameter of bandage roll 30 so that the body of foam chemicals 18 is spaced inwardly from the side edges of the bandage strip in order to promote ease of handling of the resultant preform, as is shown in FIG. 5.

When a preform of the desired length has been made, the handle 26 is manually released to stop flow of the foam chemicals; and the bandage strip 20 is cut transversely to provide a tail of suitable length for ease in handling of the preform. After a short period of time has expired in order to allow the urethane chemicals to commence cure, the preform is wrapped about the undergarment 14 in an overlapping spiral pattern to form the cast 10, as is shown in FIGS. 1 and 2. The injured limb is maintained immobile for a further short period of time until the urethane foam has cured completely to a rigid mass.

The canister 34 is sized to provide sufficient foam chemicals for a single medical cast or a major portion of such a cast and the various mechanical components are fabricated from inexpensive materials. Thus, the dispensing apparatus 22 may be disposed of in the trash after a single usage.

The specific embodiment herein shown and described is to be considered as being primarily illustrative. Various changes in structure will, no doubt, occur to those skilled in the art; and such changes are to be understood as forming a part of this invention insofar as they fall within the spirit and scope of the appended claims.

The invention is claimed as follows:

1. Dispensing apparatus for use in making a foam medical cast comprising: a yoke arrangement having bearing means for holding and allowing rotation of a bandage roll, said yoke arrangement further having mounting means for securing a foam chemicals canister in substantially rigid position relative to said bearing means and aligned along a longitudinal axis; and a manually operable handle, including a grip portion disposed generally parallel with said axis on one side thereof and an offset portion pivotally connected to said yoke arrangement on the opposite side of and spaced apart from said axis, said offset portion having intermediately disposed, canister valve actuating means aligned with said axis, whereby depression of said grip portion generally toward said axis imposes a substantially linear force at said canister valve actuating means for ensuring uniform deposition of foam chemicals onto bandage fabric unrolled from said roll.

2. Dispensing apparatus according to claim 1 wherein said bearing means includes a removable axle whereby to permit replacement of the bandage roll.

3. Dispensing apparatus according to claim 1 wherein said canister mounting means includes releasible fastener means for facilitating replacement of the foam chemicals canister.

4. Dispensing apparatus according to claim 1 wherein said canister mounting means includes contoured section means for matably engaging a confrontable region of a said canister.

5. Dispensing apparatus for use in making a foam medical cast comprising: a canister charged with foam-making chemicals under superatmospheric pressure and including an actuating and dispensing valve; a rolled-up strip of bandage fabric; a yoke arrangement having bearing means for holding and allowing rotation of said bandage roll, said yoke arrangement further having mounting means for securing said canister in substantially rigid position; and manually operable handle means pivotally mounted to said yoke arrangement for imposing actuating force on said valve, whereby operation of said handle to open said valve and simultaneous transit of said yoke arrangement to unroll said bandage produces a medical cast preform of foam deposited on an outstretched bandage strip.

6. Dispensing apparatus according to claim 5 wherein said canister valve is arranged to be depressibly actuatable and wherein said handle means is arranged to impose a linear actuating force on said valve.

7. Dispensing apparatus according to claim 5 wherein said canister valve includes a fan-shaped discharge nozzle disposed generally transverse the strip of bandage fabric.

8. Dispensing apparatus for use in making a foam medical cast comprising: a canister charged with foam-making chemicals under superatmospheric pressure and including an actuating and dispensing valve; a yoke arrangement having mounting means gripped about a portion of the canister to hold said canister in substantially rigid position with said valve aligned to discharge foam chamicals generally along a horizontal axis, said yoke arrangement further including bearing means and a strip material storage roll rotatably mounted on said bearing means generally transverse said longitudinal axis; a length of strip material wound on said roll; and manually operable handle means for imposing linear actuating force on said valve, whereby operation of said handle means to open said valve coupled with simultaneous transport of said yoke arrangement across a horizontal support surface to unroll strip material from said storage roll produces an elongated bead of foam assembled with a length of said strip material preliminary to the making of a foam medical cast.

* * * * *